United States Patent
Vitushinsky et al.

(10) Patent No.: US 8,795,511 B2
(45) Date of Patent: Aug. 5, 2014

(54) CONFIGURATION, A SENSING ELEMENT WITH SUCH CONFIGURATION, ELECTROCHEMICAL SENSOR COMPRISING SUCH SENSING ELEMENT AND METHOD FOR ELECTROCHEMICAL SENSING USING SUCH ELECTROCHEMICAL SENSOR

(75) Inventors: Roman Vitushinsky, Vaals (NL); Mercedes Crego Calama, Geldrop-Mierlo (NL); Sywert Brongersma, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 0 days.

(21) Appl. No.: 13/354,174

(22) Filed: Jan. 19, 2012

(65) Prior Publication Data

US 2012/0181185 A1 Jul. 19, 2012

Related U.S. Application Data

(60) Provisional application No. 61/434,241, filed on Jan. 19, 2011.

(51) Int. Cl.
*H01L 29/778* (2006.01)
*G01N 27/26* (2006.01)
*G01N 27/414* (2006.01)

(52) U.S. Cl.
CPC .......... *H01L 29/778* (2013.01); *G01N 27/4141* (2013.01)
USPC ........... 205/775; 204/424; 257/253; 257/194; 257/E29.246; 73/31.06

(58) Field of Classification Search
CPC .......................... G01N 27/4141; H01L 29/778
USPC .................. 204/775; 257/253, 194, E29.246; 73/31.06
See application file for complete search history.

(56) References Cited

U.S. PATENT DOCUMENTS 4,568,444 A * 2/1986 Nakamura et al. ............ 257/253
(Continued)

FOREIGN PATENT DOCUMENTS

EP 2003444 A1 12/2008
(Continued)

OTHER PUBLICATIONS

"Electrochemical Methods: Fundamentals and Applications", 1980, by John Wiley & Sons, Inc.*

(Continued)

*Primary Examiner* — Luan Van
*Assistant Examiner* — Steven Rosenwald
(74) *Attorney, Agent, or Firm* — Knobbe Martens Olson & Bear LLP

(57) ABSTRACT

A configuration is disclosed. In one aspect, the configuration includes a substantially planar electrode layer, in a first plane. The configuration further includes a substantially planar two-dimensional electron gas (2DEG) layer electrically connected in series with the electrode layer. The 2DEG layer is provided in a second plane substantially parallel with the first plane and located at a predetermined distance, in a direction orthogonal to the first plane, from the first plane. The 2DEG layer and the electrode layer are patterned such that the electrode layer overlays a part of the 2DEG layer, wherein the predetermined distance between the first plane and the second plane is selected to be sufficiently small for allowing electrostatic interaction between the electrode layer and the 2DEG layer.

18 Claims, 3 Drawing Sheets

(56) References Cited

U.S. PATENT DOCUMENTS

| | | | |
|---|---|---|---|
| 5,431,883 A * | 7/1995 | Barraud | 422/82.01 |
| 7,403,113 B2 * | 7/2008 | Moon et al. | 340/539.22 |
| 2005/0263790 A1 | 12/2005 | Moon et al. | |
| 2008/0203431 A1 * | 8/2008 | Garcia et al. | 257/192 |

FOREIGN PATENT DOCUMENTS

| | | | |
|---|---|---|---|
| EP | 2096675 A1 | 9/2009 | |
| WO | WO 2009/039298 A2 | 3/2009 | |
| WO | WO 2010/005738 A1 | 1/2010 | |

OTHER PUBLICATIONS

European Search Report for European Patent Application No. 12151470.7-1240 issued Jun. 6, 2012 by European Patent Office.

* cited by examiner

CONFIGURATION, A SENSING ELEMENT WITH SUCH CONFIGURATION, ELECTROCHEMICAL SENSOR COMPRISING SUCH SENSING ELEMENT AND METHOD FOR ELECTROCHEMICAL SENSING USING SUCH ELECTROCHEMICAL SENSOR

CROSS REFERENCE TO RELATED APPLICATIONS

This application claims priority under 35 U.S.C. §119(e) to U.S. provisional patent application 61/434,241 filed on Jan. 19, 2011, which application is hereby incorporated by reference in its entirety.

BACKGROUND OF THE INVENTION

1. Field of the Invention

The disclosed technology relates to a configuration, a sensing element with such configuration, an electrochemical sensor comprising such a sensing element and a method for electrochemical sensing using such an electrochemical sensor.

2. Description of the Related Technology

Electrochemical sensing relies on oxidation reactions or reduction reactions involving a target analyte (a gas or a liquid), at an electrode/electrolyte interface. The established electrochemical potentiometric and amperometric sensors are physically limited in sensitivity, response dynamic and selectivity due to the electrode created potentials and redox processes taking place at the electrode/electrolyte interface. Sensor miniaturization additionally causes a smaller signal, a reduced selectivity and sensitivity, an increase of the noise level, and reduces the long term stability.

In two-electrode potentiometric sensors the difference in electrochemical potential between a reference electrode and a working electrode is measured while no current is flowing in the electrolyte between the electrodes. In amperometric sensors (usually comprising three electrodes) a current is flowing between a working electrode and a counter electrode through the electrolyte.

Electrochemical sensors with good sensitivity have been reported based on ion sensitive field effect transistors (ISFETs), e.g. GaN/AlGaN ISFETs, having an open gate in direct contact with the electrolyte. For such ISFET based devices, sensing is based on monitoring a conductivity change of the source-drain channel. They operate in a pseudo-amperometric mode, wherein a current is flowing between a source and a drain of the transistor (not through the electrolyte). These GaN/AlGaN-based electrochemical sensors are relatively complex and the pseudo-amperometric mode leads to relatively high power consumption. The ISFET-mode excludes established electrochemical two- and three-electrode layouts thus preventing potentiometric low power implementations.

GaN/AlGaN 2DEG-based electrochemical ISFET-sensors are much more sensitive compared to non-2DEG-based electrochemical sensors. This is related to the very high sensitivity of the two dimensional electron gas (transistor channel) to any surface potential charge, which electrostatically interacts with the electrons in the channel and thereby modulates the 2DEG-channel resistance. Surface charge may be generated by e.g. redox processes involving a functional layer deposited at the surface, by diverse molecular getter-effects or by an electrochemical double-layer at the surface/electrolyte interface. These devices can be used for sensing of gases, polar molecules, (bio-)molecules or (bio-)reactions, pH, and the concentration of ions in solutions.

A drawback of such (2DEG) ISFET based configurations is that they require the presence of a source-drain current for sensing, such that they do not allow zero-current, and thus zero-power, potentiometric applications.

SUMMARY OF CERTAIN INVENTIVE ASPECTS

Certain inventive aspects relate to 2DEG based electrochemical gas sensors that can be miniaturized, that have a high sensitivity, a good response dynamic, good resolution and a good selectivity, and that can operate in potentiometric mode or in amperometric mode.

One inventive aspect relates to an electrochemical sensor comprising at least one sensing element, the at least one sensing element comprising a substantially planar working electrode in a first plane. The sensing element further comprises a substantially planar 2DEG layer electrically connected in series with the working electrode, the 2DEG layer being provided in a second plane substantially parallel with the first plane and located at a predetermined distance, in a direction orthogonal to the first plane, from the first plane. The 2DEG layer and the working electrode are patterned such that the working electrode overlays a, preferably major, part of the 2DEG layer. The 2DEG layer may be present underneath a, preferably major, part of the working electrode. The predetermined distance between the first plane and the second plane is selected to be sufficiently small, for example in the range between about 5 nm and 25 nm, for allowing electrostatic interaction between the working electrode and the 2DEG layer.

In the context of the current application, major part means more than half of the area. So, for example, major part of the working electrode preferably means more than half of the area of the working electrode and thus for example, preferably, the working electrode overlays more than half of the area of the 2DEG layer and/or for example, preferably, the 2DEG layer is present underneath more than half of the area of the working electrode.

It has been found that when the 2DEG layer and the working electrode are patterned such that the working electrode overlays a major part of the 2DEG layer, the electrostatic interaction between the working electrode and the 2DEG layer are increased such that the sensitivity of the sensing element and therefore the electrochemical sensor increase as the working electrode in such configuration has been found to operate as gate-electrode providing an electro-magnetic depletion or enhancement function modulating the resistivity of the 2DEG layer.

The working electrode and the 2DEG layer should preferably, next to the electrical connection providing the serial connection between the working electrode and the 2DEG layer, not be electrically interconnected. Thereto, for example an electrically insulating layer can be present between the working electrode and the 2DEG layer while still allowing the working electrode and the 2DEG layer to be serially interconnected.

In one aspect, the working electrode overlays the 2DEG layer and extends beyond at least part of the 2DEG layer, particularly with a distance of between about 0-100 micrometer, to further increase the electrostatic interaction between the working electrode and the 2DEG layer.

The working electrode and the 2DEG layer should preferably, next to the electrical connection providing the serial connection between the working electrode and the 2DEG layer, not be electrically interconnected. Thereto, for example an electrically insulating layer can be present between the working electrode and the 2DEG layer while still allowing the working electrode and the 2DEG layer to be serially interconnected, for example by, as explained below, a first electrode extending through the insulating layer.

In one aspect, the working electrode is in electrical contact with a first electrode, for example applied through the electrically insulating layer, providing an electrical connection between the working electrode and the 2DEG layer.

In one aspect, the 2DEG layer is in electrical contact with a second electrode, for example applied through the electrically insulating layer, providing an electrical connection between the 2DEG layer and a contact layer.

In one aspect, the first and the second electrode are electrically connected to each other through the 2DEG layer.

In one aspect, the working electrode does not directly contact the second electrode and for example sufficient distance, for example at least about 1 micrometer, is left between the working electrode and the second electrode such as to avoid direct electric currents, electric shortcut currents, from the working electrode to and from the second electrode.

Such configuration, as used in for example the sensing element, comprising an electrode parallel with a 2DEG layer, at a predetermined distance from the 2DEG layer allowing electrostatic interaction, and electrically connected in series with the 2DEG layer is further referred to as a '2DEG modulated electrode'.

A sensing element of an electrochemical sensor may further comprise additional electrodes, e.g. at least one reference electrode and/or at least one counter electrode. At least part of these additional electrodes may have a 2DEG modulated electrode configuration as described above.

An electrochemical sensor may comprise a plurality of sensing elements, e.g. an array of sensing elements.

It is an advantage of an electrochemical sensor in one aspect that it can be miniaturized, that it can have a very high sensitivity and that it can be used in a potentiometric mode. Therefore, an electrochemical sensor may advantageously be used in low power or zero power applications.

In one aspect, the sensing element comprises a heterojunction structure comprising a stack of a first layer and a second layer, wherein the heterojunction structure is selected such that a two-dimensional electron gas (2DEG) layer is formed at the interface between the first layer and the second layer. The working electrode can be provided directly on top of the second layer, such that the predetermined distance between the working electrode and the 2DEG layer corresponds to a thickness of the second layer. In one aspect, additional layers can be present between the second layer and the working electrode. The sensing element can, for example further, comprise a first electrode electrically connecting the working electrode and the 2DEG layer in series. It can, for example further, comprise a second electrode electrically connecting the 2DEG layer to a contact layer. The sensing element may further comprise at least one reference electrode and/or at least one counter electrode.

One inventive aspect relates to a method for electrochemical sensing using an electrochemical sensor, wherein the method comprises: providing an electrochemical sensor as described herein.

One inventive aspect relates to a potentiometric method for electrochemical sensing using an electrochemical sensor according to the first aspect, wherein the method comprises: providing an electrochemical sensor according to the first aspect, wherein the sensor comprises a 2DEG modulated working electrode and a reference electrode at a sensor surface; bringing at least the sensor surface into contact with an electrolyte; and measuring a potential difference between the working electrode and the reference electrode. Changes occurring in the electrolyte, e.g. related to the presence of an analyte to be detected, result in changes of the potential difference between the working electrode and the reference electrode. These changes are a measure for the presence and/or concentration of the analyte to be detected.

One inventive aspect relates to an amperometric method for electrochemical sensing using an electrochemical sensor according to the first aspect, wherein the method comprises: providing an electrochemical sensor according to the first aspect, wherein the sensor comprises a 2DEG modulated working electrode, at least one reference electrode and at least one counter electrode at a sensor surface; bringing at least the sensor surface into contact with an electrolyte; applying a potential difference between the working electrode and the at least one reference electrode; and measuring a current between the working electrode and the at least one counter electrode.

One inventive aspect relates to a configuration comprising a substantially planar electrode layer, e.g. metal layer, in a first plane. The 2DEG modulated electrode further comprises a substantially planar 2DEG layer electrically connected in series with the electrode layer, the 2DEG layer being provided in a second plane substantially parallel with the first plane and located at a predetermined distance, in a direction orthogonal to the first plane, from the first plane. The 2DEG layer and the electrode layer are patterned such that the electrode layer overlays a part, preferably a major part, of the 2DEG layer and thus, preferably, the electrode layer overlays more than half of the area of the 2DEG layer. Preferably the 2DEG layer is present underneath a part, preferably a major part, of the electrode layer and thus, preferably, the 2DEG layer is present underneath more than half of the area of the electrode layer. The predetermined distance between the first plane and the second plane is selected to be sufficiently small, for example in the range between about 5 nm and 25 nm, for allowing electrostatic interaction between the electrode layer and the 2DEG layer.

Such configuration is further also referred to as a '2DEG modulated electrode'.

It has been found that when the 2DEG layer and the electrode are patterned such that the electrode layer overlays a major part of the 2DEG layer, the electrostatic interaction between the electrode layer and the 2DEG layer are increased such that the sensitivity of the sensing element and therefore the electrochemical sensor increase.

In one aspect, the electrode layer overlays the 2DEG layer and extends beyond at least part of the 2DEG layer, particularly with a distance of between about 0-100 micrometer, to further increase the electrostatic interaction between the electrode layer and the 2DEG layer.

The electrode layer and the 2DEG layer should preferably, next to the electrical connection providing the serial connection between the electrode layer and the 2DEG layer, not be electrically interconnected. Thereto, for example an electrically insulating layer can be present between the electrode layer and the 2DEG layer while still allowing the electrode layer and the 2DEG layer to be serially interconnected, for example by, as explained below, a first electrode extending through the insulating layer.

In one aspect, the electrode layer is in electrical contact with a first electrode, for example applied through the electrically insulating layer, providing an electrical connection between the electrode layer and the 2DEG layer.

In one aspect, the 2DEG layer is in electrical contact with a second electrode, for example applied through the electrically insulating layer, providing an electrical connection between the 2DEG layer and a contact layer.

In one aspect, the first and the second electrode are electrically connected to each other through the 2DEG layer.

In one aspect, the electrode layer does not directly contact the second electrode and for example sufficient distance, for example at least 1 micrometer, is left between the electrode layer and the second electrode such as to avoid direct electric currents, electric shortcut currents, from the electrode layer to and from the second electrode.

Certain objects and advantages of various inventive aspects have been described herein above. Of course, it is to be understood that not necessarily all such objects or advantages may be achieved in accordance with any particular embodiment of the disclosure. Thus, for example. those skilled in the art will recognize that the disclosure may be embodied or carried out in a manner that achieves or optimizes one advantage or group of advantages as taught herein without necessarily achieving other objects or advantages as may be taught or suggested herein. Further, it is understood that this summary is merely an example and is not intended to limit the scope of the disclosure as claimed. The disclosure, both as to organization and method of operation, together with features and advantages thereof, may best be understood by reference to the following detailed description when read in conjunction with the accompanying drawings.

BRIEF DESCRIPTION OF THE DRAWINGS

FIG. 1(a): cross section; FIG. 1(b): top view.

FIG. 2 schematically illustrates an electrochemical sensing element according to one embodiment, wherein the electrochemical sensing element can operate in a three-electrode amperometric mode.

Figure 1:
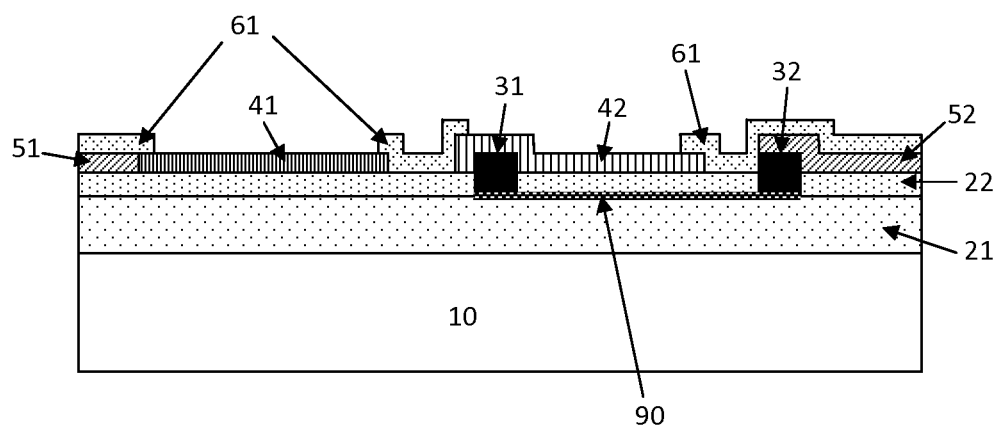
FIG. 1 schematically illustrates an electrochemical sensing element according to one embodiment, wherein the electrochemical sensing element can operate in a two-electrode potentiometric mode.
Figure 1:
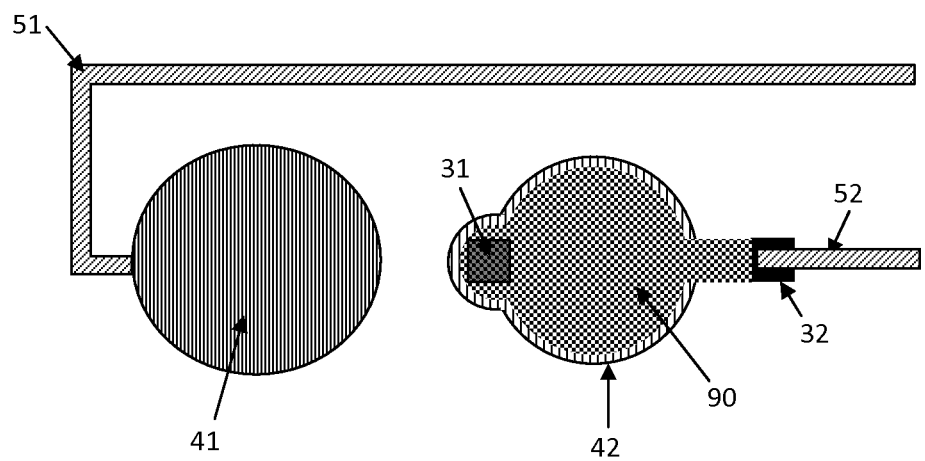

Any reference signs in the claims shall not be construed as limiting the scope of the present disclosure.

In the different drawings, the same reference signs refer to the same or analogous elements.

DETAILED DESCRIPTION OF CERTAIN ILLUSTRATIVE EMBODIMENTS

In the following detailed description, numerous specific details are set forth in order to provide a thorough understanding of the disclosure and how it may be practiced in particular embodiments. However, it will be understood that the present disclosure may be practiced without these specific details. In other instances, well-known methods, procedures and techniques have not been described in detail, so as not to obscure the present disclosure. While the present disclosure will be described with respect to particular embodiments and with reference to certain drawings, the disclosure is not limited hereto. The drawings included and described herein are schematic and are not limiting the scope of the disclosure. It is also noted that in the drawings, the size of some elements may be exaggerated and, therefore, not drawn to scale for illustrative purposes.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

FIG. 1 schematically illustrates a sensing element of an electrochemical sensor according to one embodiment, wherein the electrochemical sensing element operates in a two-electrode potentiometric mode. The electrode configuration is adapted to enable current free (and thus zero power) potentiometric electrochemical measurements with a 2DEG channel. FIG. 1(a) shows a cross section of the sensing element. The electrochemical sensing element illustrated in FIG. 1(a) comprises a heterojunction structure comprising a stack of a first layer 21 and a second layer 22, the stack being provided on a substrate 10. The first layer 21 and the second layer 22 are selected for enabling the creation of a 2DEG layer 90 at their interface. Any material combination that allows creating a heterojunction with confined 2DEG can be used for forming these layers, such as for examples Group III-V materials. In order to influence the 2DEG properties they can be doped (for example with silicon) or they can be undoped. The first layer 21 can for example be a GaN layer with a thickness in the range between about 0.1 micrometer and 3 micrometer. The second layer 22 can for example be an AlGaN layer with a thickness in the range between about 5 nm and 25 nm. However, the present disclosure is not limited thereto and any other suitable materials and layer thicknesses known to a person skilled in the art can be used. The 2DEG layer 90 is patterned, for example by etching back of the second layer 22 or by ion implantation or by any suitable method known to a person skilled in the art. Patterning of the 2DEG layer 90 is such that the working electrode (described further) overlays a major part of the 2DEG layer 90. The substrate 10 can for example comprise Si, SiC, AlN, GaN, sapphire or any other suitable material known to a person skilled in the art. On top of and in contact with the 2DEG layer 90, a first electrode 31 is provided. The sensing element further comprises a working electrode 42 in electrical contact with the first electrode 31. Thus, the first electrode 31 provides an electrical connection between the working electrode 42 and the 2DEG layer 90. The working electrode 42 can for example consist of or comprise IrOx, Au, IrPt or any other suitable material known to a person skilled in the art. In addition, the sensing element shown in FIG. 1 comprises a reference electrode 41, e.g. an Ag/AgCl reference electrode. A first contact layer 51, e.g. a Au contact layer, is provided for electrically contacting the reference electrode 41. The sensing element further comprises a second electrode 32 in contact with the 2DEG layer 90, such that an electrical series connection is established between the second electrode 32 and the working electrode 42, through the 2DEG layer 90 and the first electrode 31. A second contact layer 52, e.g. a Au contact layer, is provided for electrically contacting the second electrode 32. Furthermore, a passivation layer 61 is provided, covering a top surface of the sensing element such that only the reference electrode 41 and the working electrode 42 are exposed to the environment. The passivation layer 61 is preferably a water resistant, dielectric layer comprising for example a polymer, a polyimide, an epoxy, BCB, SU8, a silicon oxide or a silicon nitride.

FIG. 1(b) shows a partial (i.e. not showing all features) top view of the sensing element. In FIG. 1(b) the working electrode 42 is shown transparent, for illustrating the shape and position of the patterned 2DEG layer 90 relative to the working electrode 42. It can be seen that the 2DEG layer 90 and the working electrode 42 are patterned such that the working electrode 42 overlays a major part of the 2DEG layer 90 and such that the 2DEG layer 90 is present underneath a major part of the working electrode 42. Only a minor part of the 2DEG layer 90 is not covered by the working electrode 42. This minor part of the 2DEG layer 90 is provided to establish an electrical connection with the second electrode 32 without creating shortcuts. In the example shown, the working electrode 42 and the reference electrode 41 have a circular shape. However, the present disclosure is not limited thereto and other suitable shapes known to a person skilled in the art van be used.

The sensing element illustrated in FIG. 1 can operate in a potentiometric mode. In case of a potentiometric operation mode there is no need for applying an external voltage to the electrodes. Upon immersing the sensing element in an electrolyte or upon bringing the top surface of the sensing element into contact with an electrolyte, a double layer compensated electrochemical surface potential is naturally formed at the interface between the electrolyte and the working electrode 42 and at the interface between the electrolyte and the reference electrode 41, depending on the electrode material and electrolyte type (ion type, ion concentration). The potentials on the reference and working electrodes are different and this potential difference is the sensor signal to be measured, between first contact layer 51 and second contact layer 52. Upon changes occurring in the electrolyte (e.g. by adding ions, changes of ion concentrations, reaction of a gas with the electrolyte) the surface potential of the reference electrode 41 remains substantially constant, while the surface potential of the working electrode 42 shifts due to changes in the ion concentrations in the electrolyte or due to surface reactions at the working electrode. Thus, the potential difference between the reference electrode 41 and the working electrode 42 changes and as a consequence the potential difference between first contact layer 51 and second contact layer 52 changes. This change in potential difference is for example a measure for an analyte (gas, liquid) concentration to be determined.

In the configuration illustrated in FIG. 1, the second contact layer (electrical gold contact) 52 is connected via the second ohmic electrode 32 to the 2DEG layer 90. Through the first electrode 31, the 2DEG layer is also connected at an opposite side to the working electrode 42, while the working electrode 42 has no direct contact to the second contact layer 52. Thus, the working electrode 42 is electrically connected to the second contact layer 52 through (in series with) the 2DEG layer 90. The plane of the 2DEG layer 90 is substantially parallel with and in close proximity to the plane of the working electrode 42. For example, the distance between the plane of the 2DEG layer and the plane of the working electrode 42 can be in the range between about 5 nm and 25 nm. Therefore an electrostatic interaction between the working electrode 42 and the 2DEG layer 90 is established. Since a 2DEG is very charge sensitive, the conductivity of the 2DEG layer is directly modulated by the surface electrochemical potential of the working electrode. A change in surface charge of the working electrode material in response to any electrochemical parametrical change of the electrolyte causes an electrostatic modulation of the underlying 2DEG layer, resulting in a changed conductivity of the 2DEG layer. This modulation of the 2DEG conductivity corresponds to a modulation of the measured potential drop between the first contact layer 51 and the second contact layer 52.

The electrochemical sensing element shown in FIG. 1 illustrates a potentiometric sensing element comprising a 2DEG modulated working electrode. In one embodiment, also the reference electrode can be operated as a 2DEG modulated electrode. This may lead to an increased response dynamic. It also allows detecting parasitic shifts of the reference electrode and it allows detecting the ionic concentration in the electrolyte.

Figure 2A:
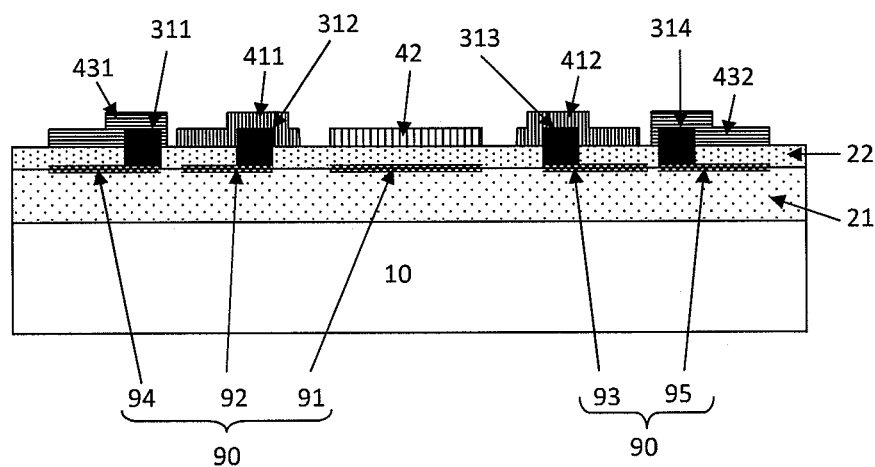
FIG. 2(a): cross section.
Figure 2B:
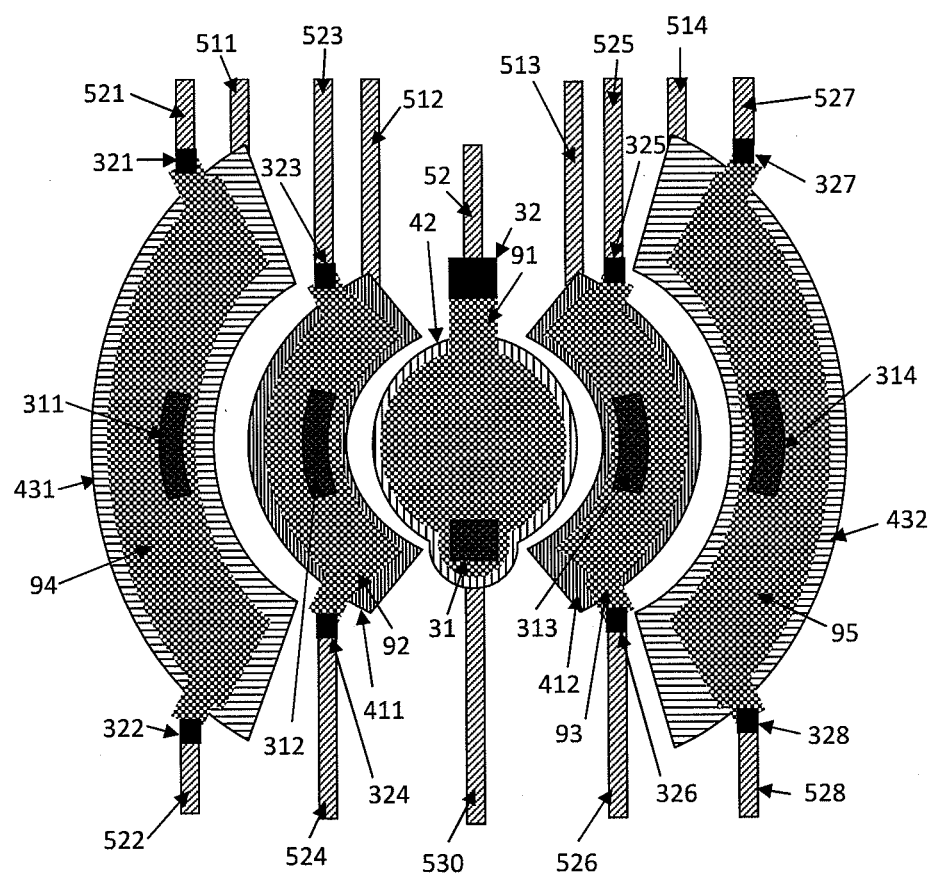
FIG. 2(b): top view.

The proposed 2DEG modulated electrode configuration as described above for electrochemical potentiometric current-free measurements can also be used in other device configurations. An example is shown in FIG. 2, illustrating an electrochemical sensing element for three-electrode amperometric measurements. FIG. 2(a) shows a cross section of a sensing element. FIG. 2(b) shows a partial (i.e. not showing all features) top view of the sensing element, wherein the electrodes (working electrode 42, reference electrodes 411, 412 and counter electrodes 431, 432) are shown transparent, for illustrating the shape and position of layers and elements underneath the electrodes. The sensing element shown in FIG. 2 can for example be used in cyclic voltammetric (CV) mode, wherein the working electrode potential is varied in a cyclic way and the corresponding current between the working electrode and a counter electrode is measured.

The electrochemical sensing element illustrated in FIG. 2 comprises a heterojunction structure comprising a stack of a first layer 21 and a second layer 22, the stack being provided on a substrate 10. The heterojunction structure is selected such that a two-dimensional electron gas (2DEG) is formed at the interface between the first layer 21 and the second layer 22. The 2DEG layer 90 is patterned, for example by etching back of the second layer 22 in appropriate areas (as described above related to FIG. 1) or by ion implantation or by any suitable method known to a person skilled in the art. The sensing element comprises a working electrode 42, a first reference electrode 411 and a second reference electrode 412, a first counter electrode 431 and a second counter electrode 432. The working electrode 42 comprises for example IrOx, Au or IrPt. The reference electrodes 411, 412 are for example Ag/AgCl reference electrodes. The counter electrodes 431, 432 can for example comprise Pt. As can be seen in FIG. 2(a), in the embodiment shown the 2DEG layer 90 consists of five separate areas, one for each of the electrodes. The first reference electrode 411 is electrically connected to 2DEG layer 92 through first electrical contact 312. The second reference electrode 412 is electrically connected to 2DEG layer 93 through first electrical contact 313. The first counter electrode 431 is electrically connected to 2DEG layer 94 through first electrical contact 311. The second counter electrode 432 is electrically connected to 2DEG layer 95 through first electrical contact 314. In addition, the working electrode 42 is electrically connected to 2DEG layer 91, through a first electrical contact 31 as schematically shown in FIG. 2(b)). In the example shown in FIG. 2(b), a contact layer 530 in electrical contact with the first electrical contact 31 is provided. For each of the counter and reference electrodes, two additional contacts (second electrical contacts) are provided to the underlying 2DEG layer, the second electrical contacts being connected to a second contact layer. This is illustrated in FIG. 2(b), showing second electrical contacts 321 and 322 and second contact layers 521, 522 for the first counter electrode 431; second electrical contacts 323, 324 and second contact layers 523, 524 for the first reference electrode 411; second electrical contacts 325, 326 and second contact layers 525, 526 for second reference electrode 412; and second electrical contacts 327, 328 with contact layers 527, 528 for the second counter electrode 432. For a given electrode, these two additional contacts provide an electrical contact to the corresponding 2DEG layer. For the working electrode 42, a second electrical contact 32 is provided for contacting the corresponding 2DEG layer 91. In addition, for each of the electrodes a first contact layer is provided for directly contacting the electrode: first contact layer 511 for first counter electrode 431; first contact layer 512 for first reference electrode 411; first contact layer 513 for second reference electrode 412; and first contact layer 514 for second counter electrode 432. Thus, all electrodes within the sensing element have a 2DEG modulated electrode configuration according to one embodiment.

The sensor element shown in FIG. 2 comprises two counter electrodes (first counter electrode 431 and second counter electrode 432). In operation, there is no current flow (ionic current in liquid) between the reference electrodes 411, 412 and the working electrode 42, but there is a current (through the electrolyte) between the counter electrodes 411, 412 and the working electrode 42. This current appears for example when using the cyclic voltammetry (CV) method, wherein the potential on the working electrode 42 is artificially changed in a cycle in a specified potential range (specific for all working materials and redox-reactions on them in the electrolyte). By using the 2DEG modulated electrodes for CV measurements within an electrode layout as illustrated in FIG. 2, a much more dynamic and stronger potential drop of the resulting electrode potentials can be achieved as compared to conventional three-electrode sensors. During CV measurements there are much more intensive redox-reactions on the surface as compared to two-electrode potentiometric measurements, thus allowing—in combination with 2DEG layers—an ultra high sensitivity. This approach allows exclusion of parasitic artifacts such as reference electrode drift and electrode corrosion during the measurements. In the configuration shown in FIG. 2, the electrical contacts 322, 324, 326, 328, 31, 321, 323, 325, 327, 32 to the 2DEG with corresponding contact layers 522, 524, 526, 528, 530, 521, 523, 525, 527, and 52 respectively allow operation in an ISFET mode for corrosion monitoring of the electrodes 411, 412, 42, 431, 432 and for the degradation monitoring of first reference electrode 411 and second reference electrode 412.

Taking into account that the 2DEG response time is in the ns range, a very wide range of CV scan rates can be used. This allows realization of the principle of time resolved selectivity providing a differentiation between diverse analytes that are simultaneously present in the solution. The principle is based on the detection of different analytes through their different characteristic redox dynamics on the electrolyte/electrode interface within the proposed sensing element.

The proposed design is fully scalable, arrayable and integratable using standard microfabrication techniques. Hence, selectivity can be obtained through differential measurements and multivariate signal analysis using scan rate spectrometry from multiple electrode functionalization layers.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A sensing element comprising:
   a substantially planar electrode layer in a first plane being a first working layer electrode; and
   a substantially planar two-dimensional electron gas (2DEG) layer electrically connected in series with the electrode layer, the 2DEG layer being provided in a second plane substantially parallel with the first plane and located at a predetermined distance, in a direction orthogonal to the first plane, from the first plane, the 2DEG layer and the electrode layer being patterned such that the electrode layer overlays a part of the 2DEG layer, wherein the predetermined distance between the first plane and the second plane is dimensioned for allowing electrostatic interaction between the electrode layer and the 2DEG layer; and
   a first electrode in direct electrical connection with the first working layer electrode and the 2DEG layer.

2. The sensing element according to claim 1, wherein the electrode layer is patterned such that the electrode layer overlays a major part of the 2DEG layer and/or wherein the 2DEG layer is present underneath a major part of the electrode layer.

3. The sensing element according to claim 1, wherein the predetermined distance between the first plane and the second plane is within the range between 5 nm and 25 nm.

4. The sensing element according to claim 1, wherein the electrode layer is a metal layer.

5. The sensing element according to claim 1, wherein the sensing element further comprises a reference electrode.

6. The sensing element according to claim 1, wherein the sensing element further comprises a counter electrode.

7. The sensing element according to claim 1, wherein the sensing element further comprises a heterojunction structure comprising a stack of a first layer and a second layer, wherein the heterojunction structure is selected such that a two-dimensional electron gas (2DEG) layer is formed at the interface between the first layer and the second layer.

8. The sensing element according to claim 7, wherein the electrode layer is provided directly on top of the second layer.

9. The sensing element according to claim 7, wherein the predetermined distance between the working electrode and the 2DEG layer corresponds to the thickness of the second layer.

10. An electrochemical sensor comprising the sensing element according to claim 1.

11. The electrochemical sensor according to claim 10, wherein the sensor comprises a plurality of sensing elements.

12. The electrochemical sensor according to claim 10, wherein the sensor comprises an array of sensing elements.

13. A method for electrochemical sensing using an electrochemical sensor, the sensor comprising a substantially planar electrode layer in a first plane, and a substantially planar two-dimensional electron gas (2DEG) layer electrically connected in series with the electrode layer, the 2DEG layer being provided in a second plane substantially parallel with the first plane and located at a predetermined distance, in a direction orthogonal to the first plane, from the first plane, the 2DEG layer and the electrode layer being patterned such that the electrode layer overlays a part of the 2DEG layer, wherein the predetermined distance between the first plane and the second plane is dimensioned for allowing electrostatic interaction between the electrode layer and the 2DEG layer, wherein the electrode layer comprises a first working layer electrode, the electrochemical sensor further comprising a first electrode in direct electrical connection with the first working layer electrode and the 2DEG layer, the method comprising:

sensing with the electrochemical sensor.

14. The method according to claim 13, wherein the method is a potentiometric method for electrochemical sensing, wherein the sensor comprises a reference electrode at a sensor surface, and wherein the method further comprises:

bringing at least the sensor surface into contact with an electrolyte; and measuring a potential difference between the working electrode and the reference electrode.

15. The method according to claim 13, wherein the method is an amperometric method for electrochemical sensing, where the sensor comprises at least one reference electrode and at least one counter electrode at a sensor surface, and wherein the method further comprises:

bringing at least the sensor surface into contact with an electrolyte;

applying a potential difference between the working electrode and the at least one reference electrode; and measuring a current between the working electrode and the at least one counter electrode.

16. The method according to claim 13, wherein the electrode layer is patterned such that the electrode layer overlays a major part of the 2DEG layer and/or wherein the 2DEG layer is present underneath a major part of the electrode layer.

17. The method according to claim 13, wherein the predetermined distance between the first plane and the second plane is within the range between about 5 nm and 25 nm.

18. The method according to claim 13, wherein the electrode layer is a metal layer.

* * * * *